United States Patent
Kuehn

(10) Patent No.: US 11,766,329 B2
(45) Date of Patent: Sep. 26, 2023

(54) ANNULOPLASTY REPAIR DEVICES, SYSTEMS AND METHODS

(71) Applicant: Stephen Kuehn, Woodbury, MN (US)

(72) Inventor: Stephen Kuehn, Woodbury, MN (US)

(73) Assignee: Serca Biomedical, LLC, Woodbury, MN (US)

(*) Notice: Subject to any disclaimer, the term of this patent is extended or adjusted under 35 U.S.C. 154(b) by 970 days.

(21) Appl. No.: 16/438,928

(22) Filed: Jun. 12, 2019

(65) Prior Publication Data

US 2019/0290429 A1    Sep. 26, 2019

Related U.S. Application Data

(63) Continuation of application No. 15/062,908, filed on Mar. 7, 2016, now Pat. No. 10,357,365.

(51) Int. Cl.
*A61F 2/24* (2006.01)

(52) U.S. Cl.
CPC .......... *A61F 2/2445* (2013.01); *A61F 2/2448* (2013.01); *A61F 2/2466* (2013.01); *A61F 2210/0014* (2013.01); *A61F 2220/0016* (2013.01); *A61F 2310/00023* (2013.01)

(58) Field of Classification Search
CPC ..................................... A61F 2/2466
See application file for complete search history.

(56) References Cited

U.S. PATENT DOCUMENTS

| | | | | |
|---|---|---|---|---|
| 5,192,291 A | * | 3/1993 | Pannek, Jr. | A61B 17/320725 606/159 |
| 2001/0020126 A1 | * | 9/2001 | Swanson | A61B 8/445 600/478 |
| 2001/0047169 A1 | * | 11/2001 | McGuckin, Jr. | A61B 10/02 606/45 |
| 2004/0127982 A1 | * | 7/2004 | Machold | A61F 2/2445 623/2.37 |
| 2007/0027456 A1 | * | 2/2007 | Gartner | A61B 17/221 606/113 |
| 2008/0228266 A1 | * | 9/2008 | McNamara | A61F 2/2445 623/2.36 |
| 2008/0306586 A1 | * | 12/2008 | Cartledge | A61F 5/0003 623/2.11 |
| 2009/0287304 A1 | * | 11/2009 | Dahlgren | A61B 17/0401 623/2.37 |
| 2011/0022038 A1 | * | 1/2011 | Seshadri | A61M 29/02 606/7 |
| 2011/0166649 A1 | * | 7/2011 | Gross | A61F 2/2466 623/2.36 |
| 2015/0272734 A1 | * | 10/2015 | Sheps | A61B 34/20 623/2.11 |
| 2015/0305869 A1 | * | 10/2015 | Styrc | A61F 2/2466 623/2.11 |

* cited by examiner

*Primary Examiner* — Leslie Lopez
(74) *Attorney, Agent, or Firm* — Anthony J. Bourget

(57) ABSTRACT

An annuloplasty prosthesis and delivery system for implanting the prosthesis adjacent an annulus of a heart valve having leaflets for adjusting the annulus to improve valve function includes a ring prosthesis made of shape memory material and having tissue attachment members which attach to the annulus in the atrium and commissural legs extending from the ring between the leaflets and secure against the underside of the valve in the ventricle. The prosthesis is carried via an orientation loop and attaches to the heart tissue such that when the prosthesis is manipulated and relaxed the annulus is adjusted to reduce or eliminate regurgitation.

37 Claims, 15 Drawing Sheets

ANNULOPLASTY REPAIR DEVICES, SYSTEMS AND METHODS

BACKGROUND OF THE INVENTION

1. Field of the Invention

The present invention relates generally to repair prostheses for implantation adjacent or upon an annulus of a heart valve and systems and methods for repair of heart valves. More particularly, it relates to annuloplasty prosthetic devices and related instruments, systems and procedures for reconstructing and remodeling a valve annulus of a person's heart.

2. Background Information

Annuloplasty prostheses, generally known as annuloplasty rings or bands, are used in conjunction with valvular reconstructive surgery to assist in the correction of heart valve defects such as stenosis and valvular insufficiency or regurgitation. Rings or bands for use in repair of both mitral and tricuspid valves are widely known. An example of an annuloplasty prostheses and related instruments and procedures for reconstructing and remodeling a valve of a person's heart include that shown in U.S. Pat. No. 8,357,195. While these and other examples have useful benefits, there is room for improvement.

SUMMARY OF THE INVENTION

An annuloplasty prosthesis having a ring body of shape memory material is flexed into positioned on or adjacent the valve annulus and released to cause a reduction in size of the valve annulus for repair. The prosthesis is a device having a ring body shaped to conform to the annulus and includes at least one tissue attachment member in cooperation with the ring body. The attachment member is configured to attach to the annulus. When the ring body is stretched, the attachment member is attached to the annulus, and when the ring body retracts, the size of the annulus is reduced and remodeled to lessen or eliminate a gap between the leaflets of the heart valve. The ring body is made of shape memory material, such as Nitinol. In aspects the ring body includes integrally attached commissure legs configured to extend between the leaflets and engage the underside (ventricle side) of the valve while securing the ring body to the annulus on the atrium side. Tissue attachment members on the ring body attach to the annulus when the ring body is flexed. Multiple commissure legs and multiple tissue attachment members may be included on the device. In one aspect the device is a unitary piece of shape memory material. In further aspects the commissure legs are self-folding and/or self-furling such that when the legs are released they retract and/or fold/roll or furl into a contracted shape in the ventricle to secure the device to the valve.

In a further aspect the invention includes a prosthesis delivery system for delivering an annuloplasty prosthesis adjacent the annulus of a heart valve. The system includes a catheter configured to be positioned within the atrium chamber of the heart, an orientation loop disposed within the catheter and configured to be expressed from the catheter where a portion of the loop is delivered through the valve to the ventricle such that a segment of the loop is oriented at a first commissure of the valve and another segment of the loop is oriented at a second commissure of the valve, and a prosthesis holder is configured to slide along the orientation loop to place a prosthesis adjacent the heart valve. A prosthesis, such as a shape memory device, may be connected to the system and positioned utilizing the delivery system. In one aspect the delivery system also includes a prosthesis slide/holder system which maintains the commissure legs of the prosthesis in an extended mode. The slide/holder system adjusts to allow the commissure legs of the prosthesis to retract or recoil or fold/furl to a shape memory state for connecting the prosthesis to the underside of the valve through the leaflets. In a further aspect the delivery system also includes a device flex mechanism for flexing or expanding the prosthesis in an anterior-posterior (or other) direction upon the valve annulus so that the prosthesis may be attached to the annulus via tissue attachment members such that upon manipulation of the flex mechanism the prosthesis retracts to its shape memory position to adjust the valve annulus. The device flex mechanism also includes a control to lock and release the prosthesis from the delivery system.

In a further aspect the invention includes a method of repairing a heart valve having leaflets and a valve annulus. The method includes delivering via a catheter a prosthesis having a ring body and self-retracting commissure legs to a location adjacent the heart valve with the legs extending between the leaflets, and releasing the self-retracting legs thereby causing the legs to be positioned at an underside of the heart valve while the ring body is positioned at an upper side of the heart valve in the atrium. The prosthesis includes tissue attachment members which attach to or adjacent the annulus. The prosthesis is flexed in the anterior-posterior direction and the attachment members are attached to the tissue such that when the prosthesis is relaxed or returned to its shape memory state the annulus is reduced and/or remodeled and the leaflets are drawn together for improved heart function.

The above partial summary of the present invention is not intended to describe each illustrated embodiment, aspect, or every implementation of the present invention. The figures and detailed description and claims that follow more particularly exemplify these and other embodiments and further aspects of the invention.

BRIEF DESCRIPTION OF THE DRAWINGS

The invention may be more completely understood in consideration of the following description of various embodiments of the invention in connection with the accompanying drawings, in which.

Figure 1:
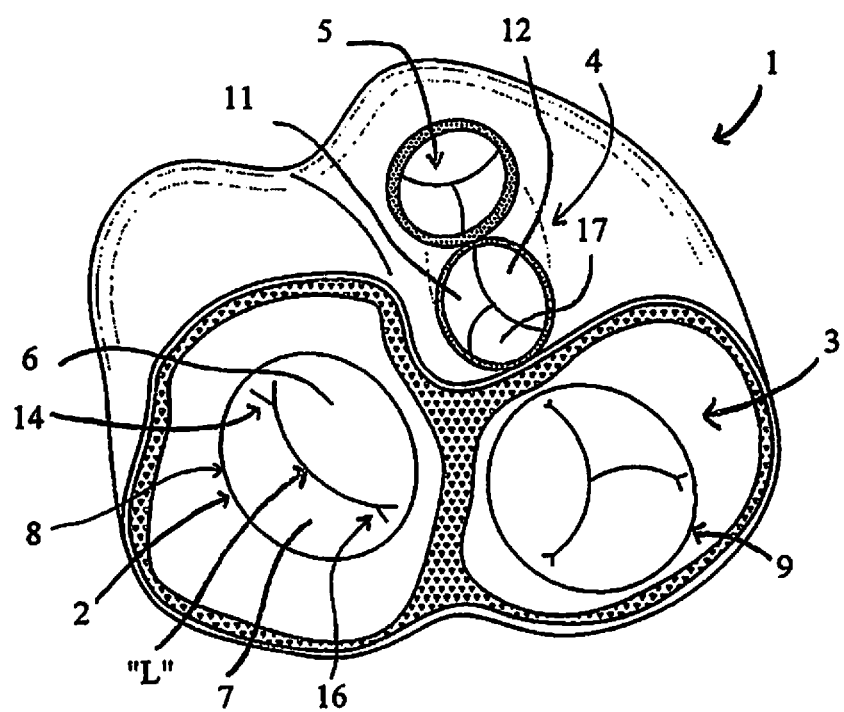
FIG. 1 is a cross-section schematic view of a heart showing heart components and valves.

While the invention is amenable to various modifications and alternative forms, specifics thereof have been shown by way of example in the drawings and will be described in detail. It should be understood, however, that the intention is not necessarily to limit the invention to the particular embodiments, aspects and features described. On the contrary, the intention is to cover all modifications, equivalents, and alternatives falling within the spirit and scope of the invention and as defined by the appended claims.

DETAILED DESCRIPTION OF THE INVENTION

Aspects of the invention pertain to an annuloplasty prosthetic ring which is used to reshape the mitral valve annulus so that the anterior and posterior leaflets of the mitral valve co-apt during ventricular contraction. Such device is utilized for treating regurgitation of a heart valve, such as the mitral valve. Further aspects involve delivery of the prosthetic ring and associated guide devices, systems and methods. Aspects include minimally-invasive catheter-based systems and methods for attaching a prosthetic ring which occurs off cardiopulmonary bypass to repair the valve of a patient's beating heart.

FIG. 1 depicts a cross-section schematic view of a human heart 1 having a mitral valve 2, tricuspid valve 3, aorta 4 and pulmonary trunk 5. Mitral valve is a bicuspid valve having an anterior cusp or leaflet 6, and a posterior cusp or leaflet 7. A mitral valve annulus 8 outlines mitral valve 2. Tricuspid valve 3 has tricuspid valve annulus 9. Aorta 4 includes a left coronary cusp 17, a right coronary cusp 12, and non-coronary cusp 11. Chordae 19 attach the leaflets to papillary muscles in the heart. Mitral valve 2 also has anterior (arterolateral) commissure 16 and posterior (posteromedial) commissure 14. Leaflet 6 and leaflet 7 of a healthy heart generally meet at a line of coaptation "L". The leaflets 6, 7 split at line L. Mitral valve 2 opens at line L to allow blood to flow from the left atrium 10 to the left ventricle 13 of heart 1.

In some disease states, blood flow can be partially occluded through the valve (stenosis), or blood flow can traverse in the opposite direction (regurgitation). Regurgitation can occur due to degenerative types of diseases of the mitral valve such as leaflet prolapse, choral rupture, and leaflet tears, and functional diseases where the leaflets remain functional but changes to the annulus such as dilation and/or conformational changes prevent leaflets from coapting during ventricular contraction. Mitral regurgitation is the most common form of heart valve disease in the United States. While there are several different types, there are two major types of mitral regurgitation—degenerative and functional. Degenerative mitral regurgitation results from a structural abnormality in some part of the valve itself, such as a damaged leaflet or broken chordae. Functional mitral regurgitation is generally caused by dilation of the mitral valve annulus such that the leaflets no longer close or seal which allows blood to flow backwards (regurgitate) through the valve. Regurgitation often occurs as the result of a heart tissue damage which leads to degeneration and enlargement of the left ventricle. Mitral regurgitation is frequently associated with heart failure which has severe physiological consequences to the patient. While the mitral valve itself is anatomically sound in functional mitral regurgitation, the valve leaks because of the damaged left ventricle and associated annulus and subannular apparatus changes.

Typically mitral valve repair and/or replacement requires open-heart surgery which carries increased risk, expense and recovery time. Open heart surgery also requires cardiopulmonary bypass (CPB) with risk of thrombosis, stroke and infarction. Due to these risks, patients with severe mitral regurgitation are denied intervention and face poor survival without correction. A percutaneous approach to the treatment of mitral regurgitation is an unmet clinical need. Such approach would allow patients to experience earlier intervention with reduced costs, reduced hospitalization, reduced health complications due to CPB and expanded treatment to more patients. Heretofore there have been no shape memory ring prostheses or associated delivery systems available for percutaneous treatment of mitral regurgitation.

Figure 2A:
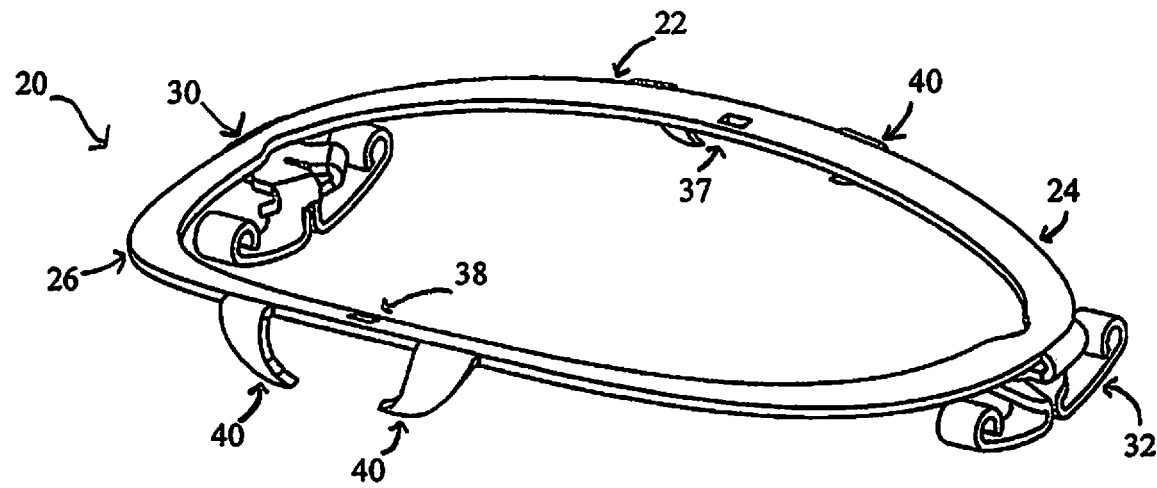
FIG. 2A is a diagram illustrating a perspective view of an adjustable prosthesis device in accordance with one aspect of the present invention.

FIG. 2A is a diagram showing an annuloplasty prosthesis or device 20 in accordance with one aspect of the present invention. Prosthesis 20 is configured to connect to the endocardial surface of the valve annulus 8. Prosthesis 20 is an expandable annuloplasty ring which may be flexed or extended in the anterior-posterior direction such that engagement of the prosthesis 20 with the native valve annulus 8 in the flexed/extended state causes the anterior leaflet 6 and posterior leaflet 7 of the valve 2 to align back to a position that supports leaflet coaptation when prosthesis 20 is in a relaxed state. Ring body 22 is configured to conform to the annulus 8 when annulus 8 is in its high stress systolic shape and to be inserted to repair the heart valve while the heart is beating. Prosthesis 20 may also be used for repair of valves in open-heart surgery. Prosthesis 20 in one aspect is utilized to repair one of the heart valves such as the mitral valve 2 or the tricuspid valve 3. The prosthesis 20 depicted in FIG. 2 is configured for repair of the mitral valve 2. Prosthesis 20 may be configured of different sizes or shapes to accommodate repair of a range of patient sizes and anatomies and other valve annulus features. Prosthesis 20 may be available in different sizes and shapes to accommodate repair of different sized or different shaped heart valves. The prosthesis is not limited to repair of the mitral valve annulus 8.

Figure 2B:
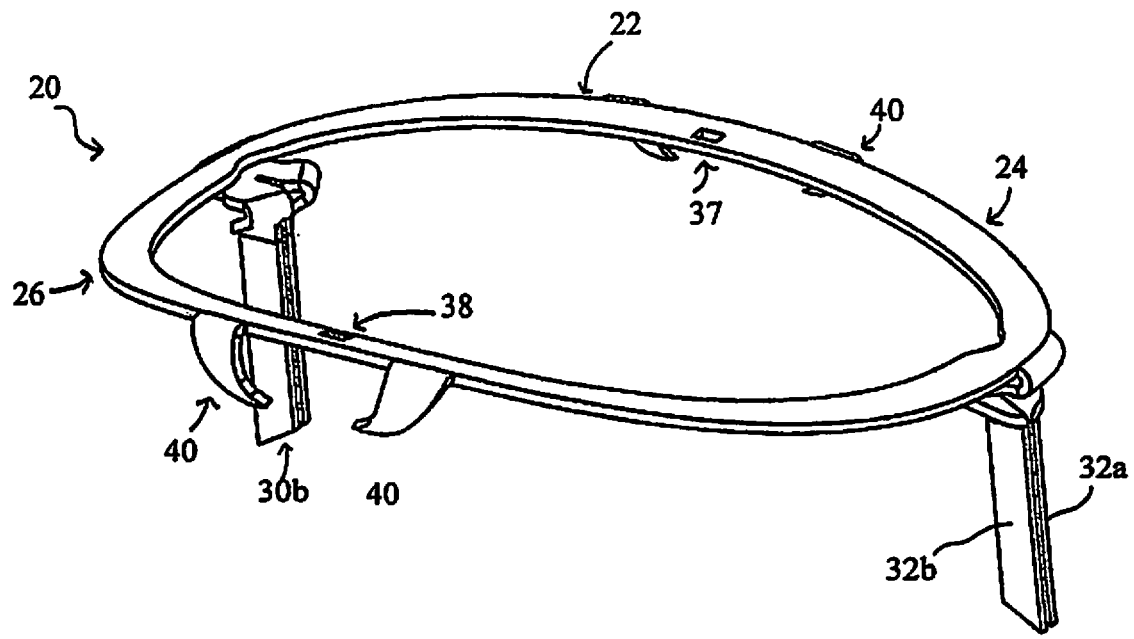
FIG. 2B is a diagram illustrating a further aspect of the device of FIG. 2A.

Device 20 is formed of a shape memory material. In one aspect prosthesis 20 is formed of NITINOL™ matter. NITINOL is a metal. Prosthesis 20 comprises a ring body 22 having a first commissure leg 30 and a second commissure leg 32. Each leg 30, 32 may be folded or rolled or furled or extended so that each leg inserts through mitral valve 2, through the line of leaflet coaptation "L" while ring body 22 remains in contact with annulus 8. FIG. 2B depicts device 20 with legs 30, 32 unfolded in part, which allows for insertion of legs 30, 32 through the valve. Each leg 30, 32 is unrolled or unfolded under the bottom of the anterior and posterior leaflets, 6, 7. The legs 30, 32 are oriented toward and rest in the sub annular groove in the ventricle while the ring body 22 is above the valve annulus 8 in the atrium. Particularly, legs 30, 32 extend from ring body 22 situated in the left atrium 10 of heart 1, through valve 2, and into the left ventricle 13 of heart 1. Leg 30 is configured to insert through posteromedial commissure 14 while leg 32 is configured to insert through anterolateral commissure 16. In one aspect device 20 includes a pair of commissure legs 30a, 30b positioned opposite commissure legs 32a, 32b. Legs 30, 32 are configured to enter the mitral valve 2 at or adjacent posteromedial commissure 14 and anterolateral commissure 16. A different number of legs 30, 32 may be used as desired.

Device 20 includes at least one tissue attachment member 40 configured to attach to the tissue of annulus 8. In one aspect attachment member 40 is a curved barb having a point such that member 40 may readily secure into tissue and be firmly set into position. The tissue attachment member 40 is not limited to a curved barb and may include attachments of different configurations or varieties. In one aspect multiple tissue attachment members 40 may be positioned adjacent each other to operate as a pair or other variety of attachment members 40. In one aspect a first pair of attachment members 40 is oriented at an anterior portion 24 of ring body 22 and a second pair of attachment members 40 is oriented at a posterior portion 26 of ring body 22. In one aspect attachment member 40 is bent into position to extend downward from ring body 22 so that it may engage the tissue or annulus 8 of valve 2. In one aspect attachment member 40 is integrally connected to ring body 22. The tissue attachment member 40 is oriented downward as are the commissure legs 30, 32.

Figure 3:
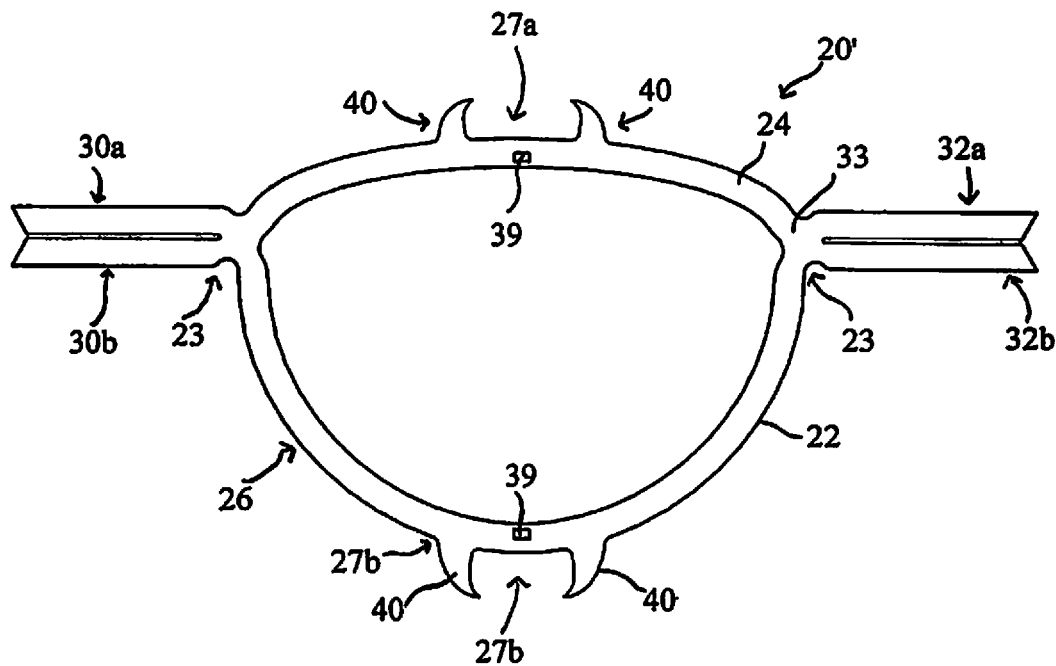
FIG. 3 is a diagram illustrating a top view of a prosthesis device in accordance with a further aspect of the present invention.
Figure 4:
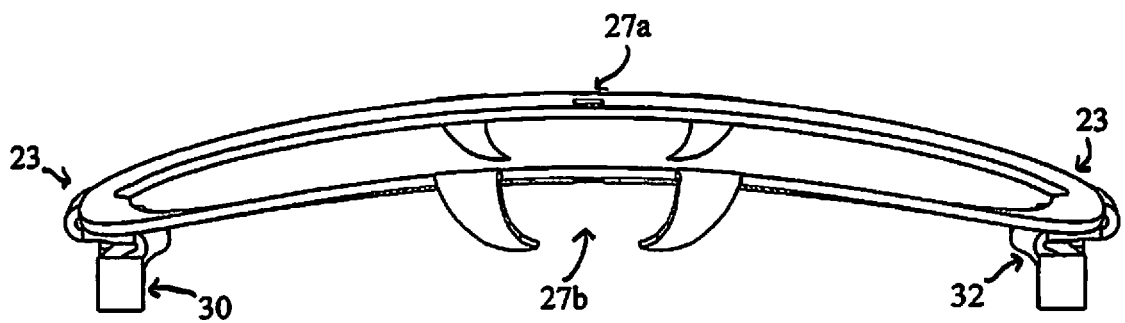
FIG. 4 is a diagram illustrating a front view of the device of FIG. 2.
Figure 5:
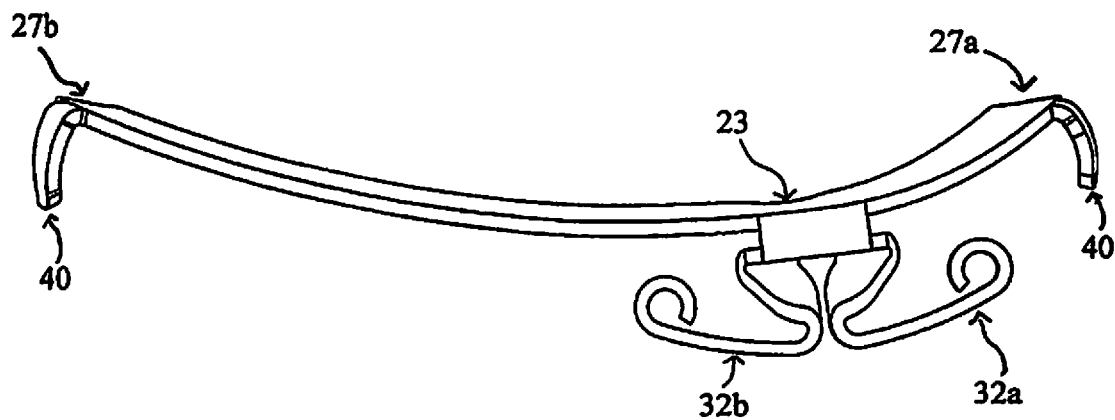
FIG. 5 is a diagram illustrating a side view of the device of FIG. 2.

FIG. 3 is a diagram illustrating a further aspect of prosthesis 20 shown as a pre-folded or flat prosthesis 20'. FIG. 3 shows device 20' in a flat configuration and prior to manipulation into the structure shown in FIG. 2. Device 20' is made of a single piece of material, such as Nitinol and formed into a desired shape. Commissure legs 30 (30a, 30b), 32 (32a, 32b) extend from ring body 22 at respective leg areas 23 of ring body 22. Commissure legs 30, 32 extend outwardly from ring body 22 at leg areas 23 and in one example are folded and/or rolled into the position shown in FIG. 2. FIG. 2 depicts device 20 in a shape memory configuration. Tissue attachment members 40 extend from ring body 22 at respective tissue attachment areas 27 of leg body 22. Tissue attachment members 40 are also folded or rolled into the position shown in FIG. 2. Additionally, in one aspect ring body 22 is formed into a generally "saddle-shaped" structure so that it may more closely resemble the natural curvature of valve 2 and annulus 8. As shown with reference to FIG. 4 and FIG. 5, ring body 22 is curved in a saddle-shaped structure such that tissue attachment areas 27 are positioned above leg areas 23 of ring body 22. Ring body 22 slopes or curves downward from tissue attachment area 27 to leg area 23. In one aspect tissue attachment area 27a is positioned at a level above tissue attachment area 27b. Commissure legs 30, 32 are also oriented closer to tissue attachment area 27a as compared to tissue attachment area 27b. Such formations are provided to better match a natural orientation of the annulus 8 of a mitral valve 2 for instance. This configured shape has the advantage of more naturally matching the shape of the annulus of a normal heart under ventricle contraction (systole). This is the condition where the mitral valve 2 is under the greatest stress as blood pumped from the ventricle presses against it. The tissue attachment areas 23 are oriented at or adjacent the posteromedial commissure 14 and anterolateral commissure 16, while the edges of respective leaflets 6, 7 come together or approach each other at a curvature depicted generally by coaptation line "L" (See FIG. 1 and FIG. 15).

Device 20 as shown in FIG. 2A and FIG. 2B is formed into shape by manipulation of flat device 20'. Particularly, flat device 20' is bent or folded or rolled or otherwise formed into the shape of device 20 and heat-set into the shape as shown. Due to the unique properties of the material comprising device 20, Nitinol for example, device 20 retains its shape until a temperature change allows the device to be temporarily reshaped. The heating changes the phase of the Nitinol to set device 20 into the desire shape shown in FIG. 2. Cooling, typically by placing device 20 in a freeze bath, changes the phase of the device allowing for device 20 to be temporarily reshaped. The device 20 may be manipulated to fit within a capsule or tube as desired (See FIG. 17, for instance). Upon a rise in the temperature the reshaped device will return to its memory state configuration shown in FIG. 2. The device 20 also has an inherent flexibility given the nature of the Nitinol and the ring shape and ability to be expanded, such as expansion in the anterior-posterior direction as stated herein. Forces may also be applied to flex device 20, and when the forces are removed the device 20 returns to a set shape. For instance, ring 22 may be over-expressed or flexed/stretched by applying force at tissue attachment area 27a, 27b to stretch anterior portion 24 away from posterior portion 26 (in the anterior-posterior direction) as described further below. When the force is released the ring will return to its natural or set state as in FIG. 2.

The curvature of device 20 also assists in the flex action or expression of device 20 in an anterior-posterior direction. In that regard, device 20 may be pulled or manipulated so that tissue attachment members 40 are set into the tissues of annulus 8, for instance, and then released so that device 20 returns to its permanent state. When released, the memory action causes device 20 to adjust (return to normal state) which in turn reshapes the annulus 8. The reshaped annulus 8 results in movement of anterior leaflet 6 and posterior leaflet 7 such that leaflets may be drawn together to correct or minimize problems with a compromised valve 2. The curvature of the device also assists with insertion of the device into the delivery system and in controlled deployment from the delivery system as noted below.

In one aspect device 20 is oriented in a permanent shape as shown in FIG. 2A and due to the nature of the shape memory properties of device 20, may be temporarily deformed and then return to the permanent state. The flat piece which comprises unformed device 20 shown in FIG. 3 may be laser cut and electro-polished to desired tolerances. Other manufacturing techniques may also be used to form device 20, including but not limited to stamping or other methods. Each of the respective legs 30, 32 may be adjusted independently of the other. Even when device 20 returns to its shape memory configuration as shown in FIG. 2, device 20 may still be flexed by applying force to ring body 22 as noted herein.

Figure 6:
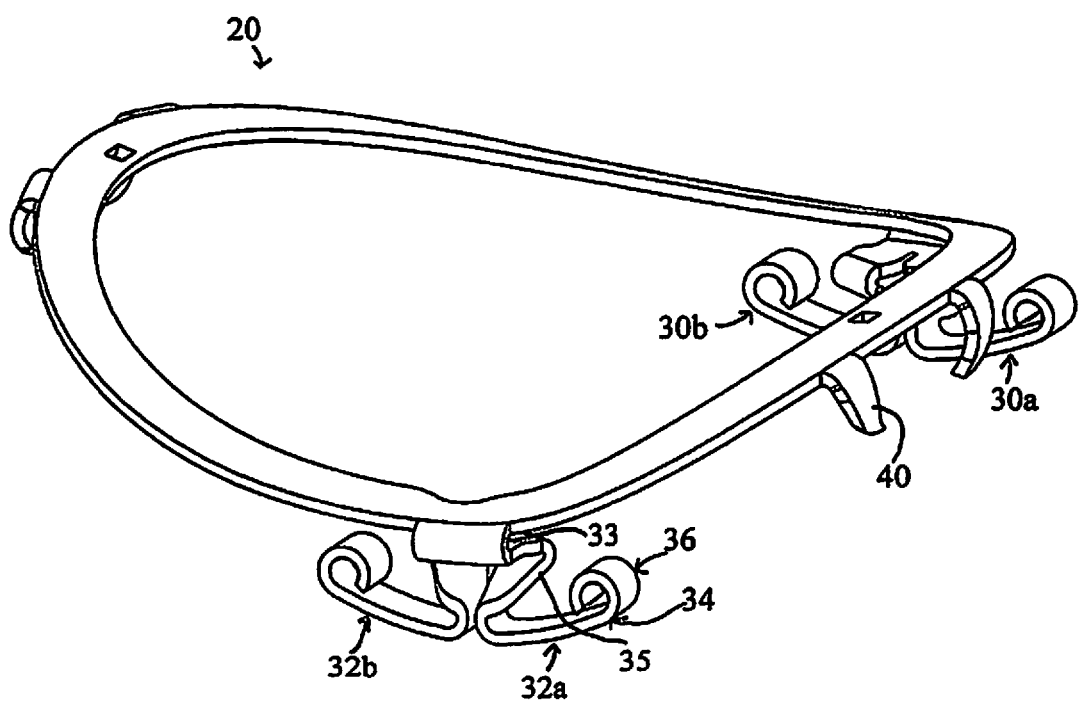
FIG. 6 is a diagram illustrating a further perspective view of the device of FIG. 2.

In one aspect, legs 30, 32, such as leg 32a, includes a series of segments which are bent into a desired configuration. As shown in FIG. 6, legs 32a, 32b are bent or curved at hip segment 33 to allow leg 32a to project downward from ring body 22. A series of bends, curves and leg segments 35 lead to a foot segment 34. At an end of foot segment 34 is provided a toe 36. In one aspect toe 36 is rolled or curled. The rolled or curled toe 36 is rolled or curled toward ring body 22, providing a relatively smooth surface for contact with the underside of leaflets 6, 7 or with sub annular groove of valve 2. Leg 32a may be flattened or at least substantial portions of leg 32a may be flattened (unfurled) for delivery to valve 2 as described in further detail below.

Figure 7:
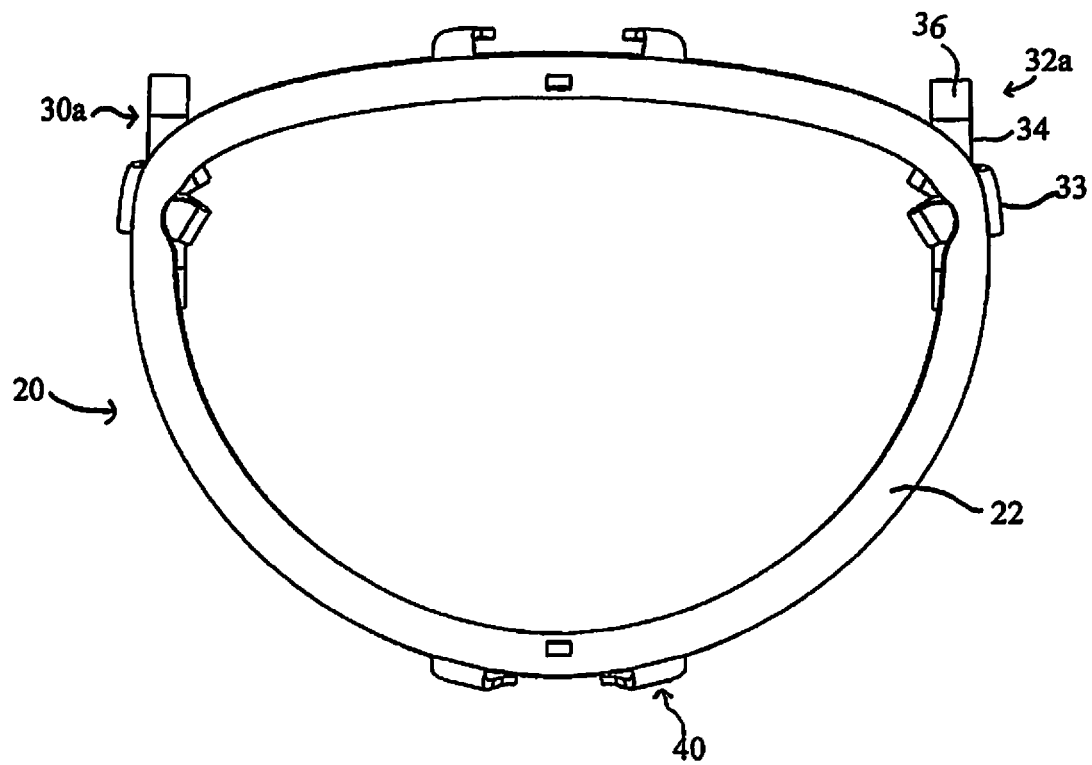
FIG. 7 is a diagram illustrating a top view of the device of FIG. 2.
Figure 8:
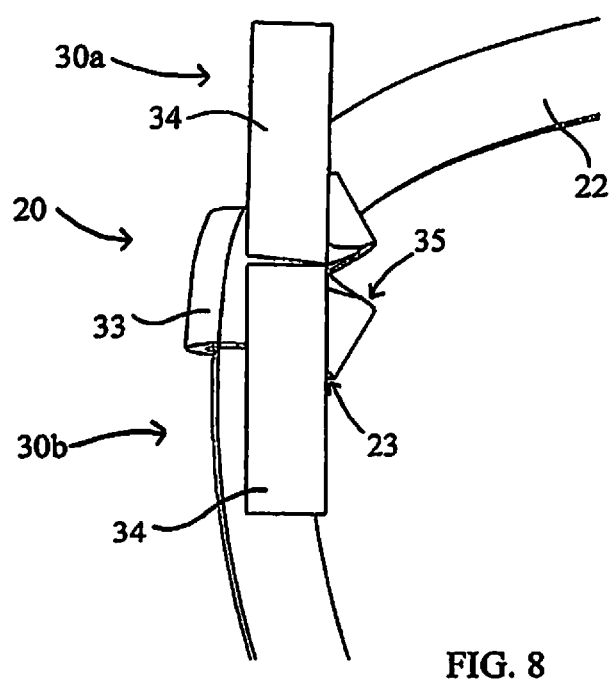
FIG. 8 is a diagram illustrating a partial bottom view of a further aspect of the present invention.

FIG. 7 is a diagram showing a top view of device 20 of FIG. 2 with legs 30, 32 and attachment members 40 folded and/or rolled. Portions of leg 32a are visible from this view which depicts foot segment 34 extending generally perpendicularly as compared to hip segment 33 (and also as compared to corresponding leg 32a of unfolded device 20' of FIG. 3). Leg 30a may be similarly configured opposite leg 32a as shown in FIG. 7. FIG. 8 is a diagram showing a bottom view of device 20 of FIG. 2 with legs 30a and 30b similarly folded. Particularly, foot segment 34 of leg 30b is oriented generally perpendicularly to hip segment 33. Foot segment 34 in this instance is also oriented generally parallel with ring body 22 adjacent leg area 23 of ring body. It may be appreciated that two legs 32a, 32b may extend from hip segment 33. It may also be appreciated that when legs 30, 32 are folded underneath ring body 22, legs 30, 32 may be placed through valve 2 and into the left ventricle of heart 1 and will secure the underside of valve 2 while ring body 22 remains in the left atrium 10 of heart 1.

Figure 9:
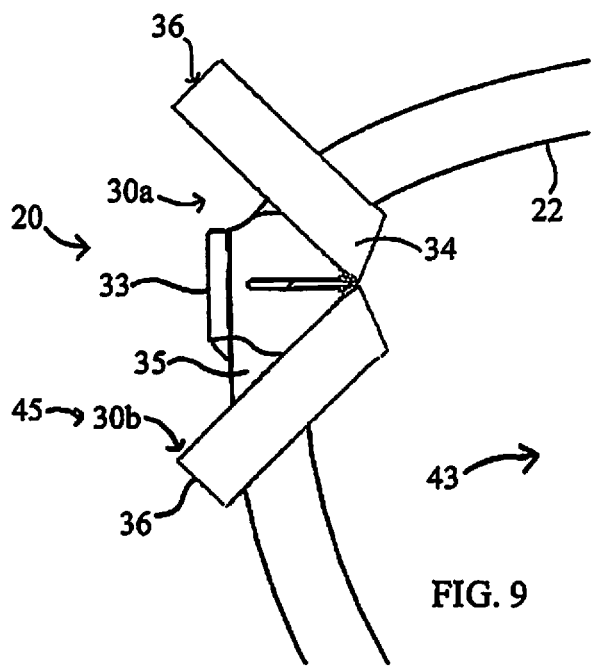
FIG. 9 is a diagram illustrating a bottom view of an alternative aspect of the present invention.
Figure 10:
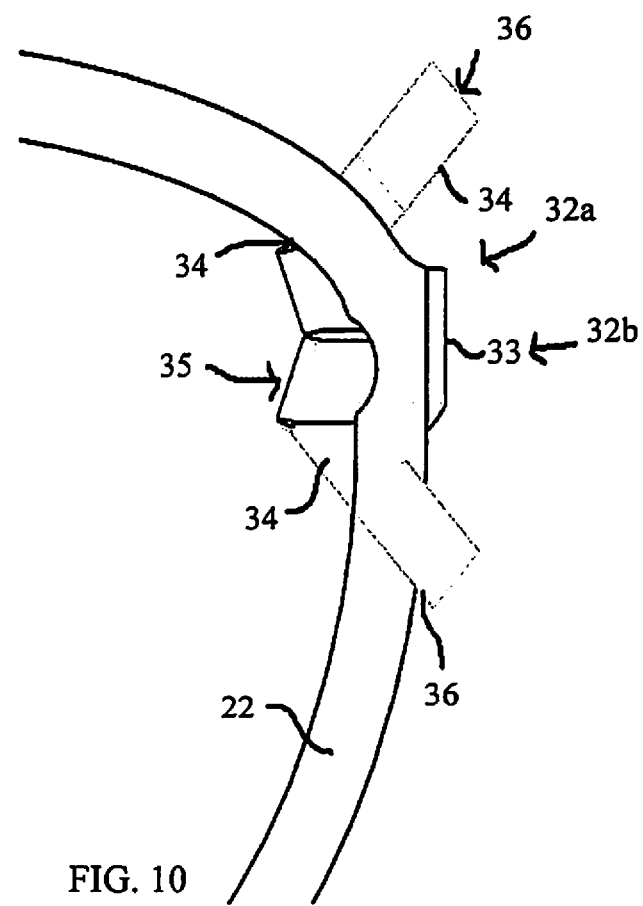
FIG. 10 is a diagram illustrating a partial top view of an alternative aspect of the present invention.

FIG. 9 is a diagram showing a bottom view of an alternative aspect of device 20 where legs 30, 32 and foot segments 34 are configured to project at different angles. For instance, segment 34 is bent such that it is angled at approximately 45 degrees with respect to hip segment 33. It may be appreciated that segments 34 may also be oriented at greater or lesser angles (other than 45 degrees) as desired, and that respective segments 34 may be oriented at different angles. As shown in FIG. 9, foot segment 34 spans from an inner field area 43 (i.e., an area within ring body 22), across ring body 22, and into outer field area 45. FIG. 10 is a diagram showing a top view of an alternative aspect of device 20 with legs 32a, 32b folded beneath ring body 22. Foot segments 34 are also angled as in FIG. 9. In this aspect toe 36 is rolled and is oriented above ring body 22, which demonstrates that segment 34 and toe 36 may be bent to provide additional friction force against the underside of annulus 8 to secure device 20 into position. In practice, segment 34 and/or toe 36 would not be positioned above ring body 22 because they would be impeded by the heart tissues (i.e., ring body 22 would be positioned in the atrium 10 above annulus 8 while segment 34 and segment 36 would be positioned in the ventricle 13 and on the underside of annulus 8).

Figure 11:
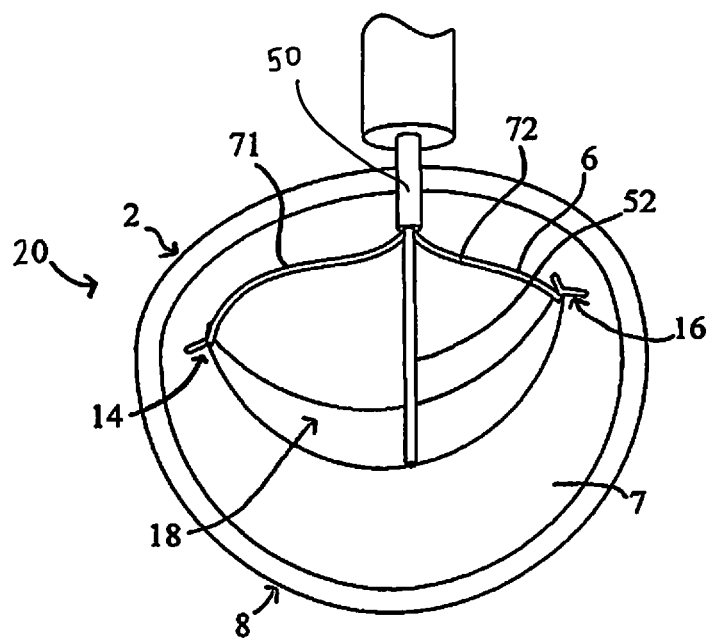
FIG. 11 is a diagram illustrating a top perspective view of a further aspect of the present invention in conjunction with features of a heart valve.
Figure 12:
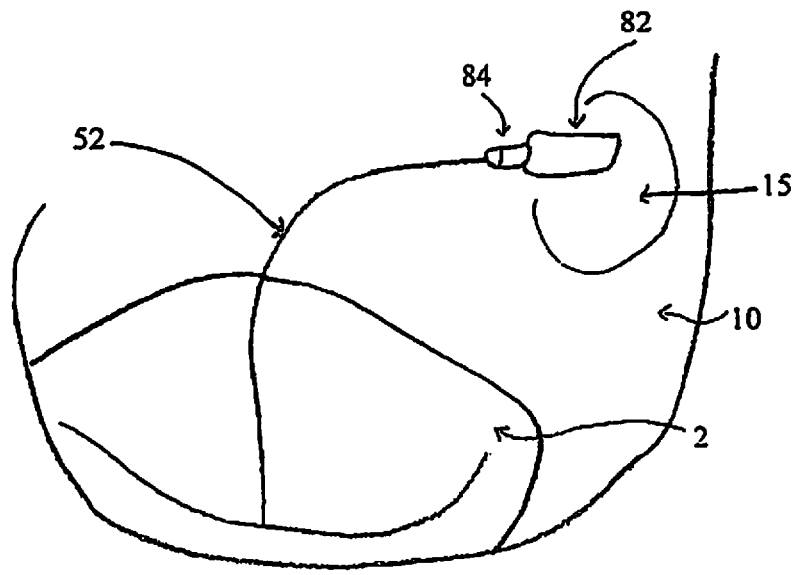
FIG. 12 is a diagram illustrating a perspective view of a further aspect of the present invention in conjunction with features of a heart.

General function or positioning of device 20 is shown throughout the figures. With reference to FIGS. 11-15, and particularly FIG. 11, valve 2 is shown where leaflets 6 and 7 do not meet, thus resulting in functional mitral regurgitation (i.e., valve 2 does not completely close, resulting in a gap 18, which causes blood to leak through gap 18 and back into the left atrium). A guidewire 52 is shown extending from an inner catheter 50. Also shown are segments 71, 72, of an orientation loop 70 (described further below) extending from catheter 50 and through gap 18 at posteromedial commissure 14 and anterolateral commissure 16. FIG. 12 is a further view of a mitral valve 2 at the base of the left atrium 10 of heart 1. Access is made to the left atrium 10 through the fossa ovalis 15 from the right atrium by an introducer 82 having a dilator 84. Particularly, a needle tip catheter may be used to pierce the fossa ovalis and thereafter guide wire 52 is positioned into the atrium, through mitral valve 2 and into ventricle 13. The needle is removed. A series of introducers 82 of varying diameters are introduced into the hole in the fossa ovalis to repeatedly expand the hole to a desired diameter for placement of catheter 60. Catheter 60 is introduced through an introducer 82 and into atrium 10. Catheter 60 may be adjusted so the opening of catheter 60 is positioned directly above mitral valve 2. The delivery system 100 is inserted through the introducer 82 over the guidewire 52 and positioned as noted herein.

Figure 13:
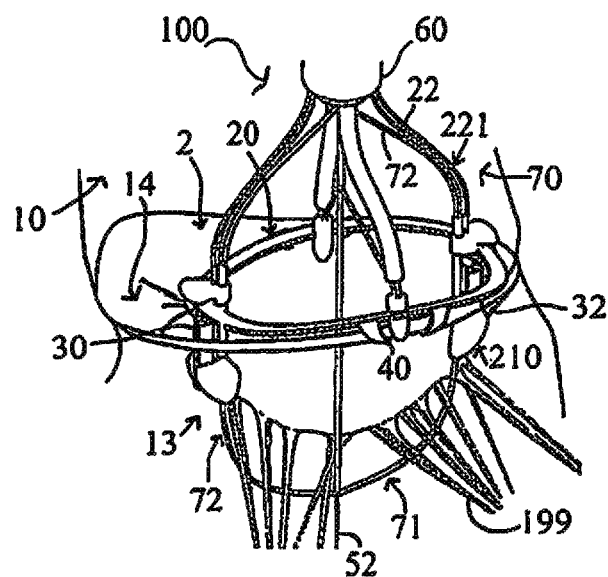
FIG. 13 is diagram illustrating a perspective view of a further aspect of the present invention in conjunction with features of a heart valve.

FIG. 13 shows one aspect of delivery system 100 with device 20 positioned at valve 2 and prior to positioning of legs 30, 32 against annulus 8 and prior to detachment of delivery system 80 from device 20. FIG. 13 shows device 20 superimposed at valve 2 and depicts orientation loop 70 with segments 71, 72 extending into left ventricle 13.

Figure 14:
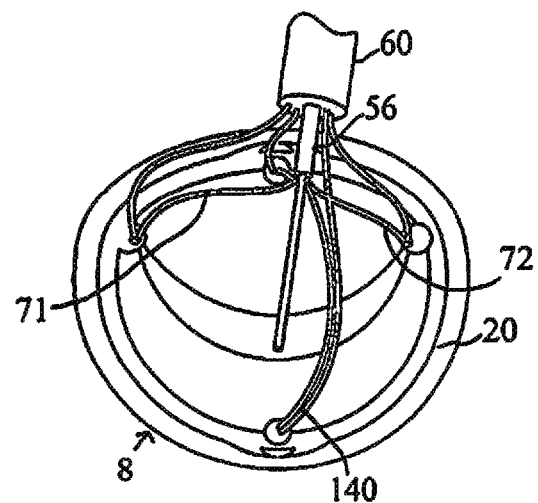
FIG. 14 is a diagram illustrating a perspective view of a further alternative aspect of the present invention in conjunction with features of a heart valve.
Figure 21:
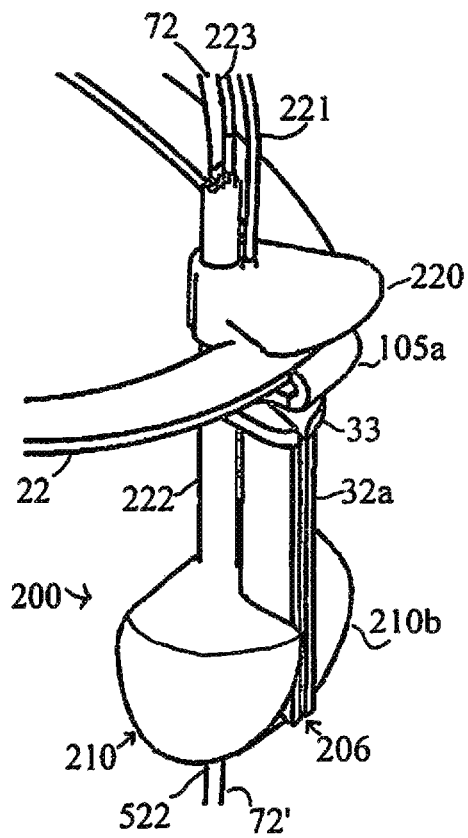
FIG. 21 is a diagram illustrating a close up view of a portion of the delivery system and slider/holder system of the present invention.
Figure 22:
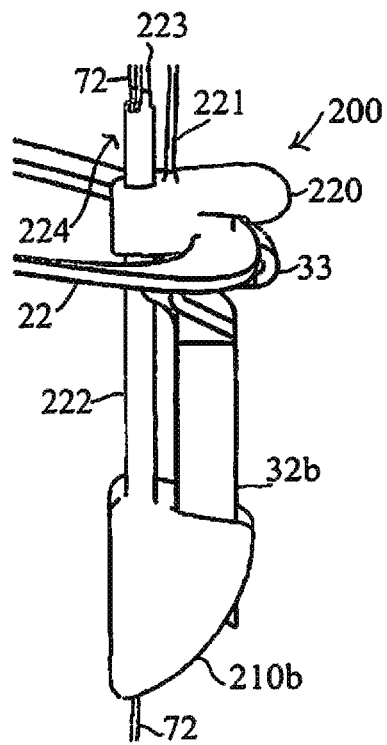
FIG. 22 is a diagram illustrating a rotated view of the aspects shown in FIG. 21.

FIG. 14 shows device 20 set into position adjacent or upon annulus 8. Legs 30, 32 are inserted through gap 18 into left ventricle 13 at commissures 14, 16 and folded underneath annulus 8 to assist in holding device 20 into desired position. Device 20 is stretched in the anterior-posterior direction to align along annulus 8. Device 20 is delivered to valve 2 via catheter 60. It may be appreciated that device 20 is stretched at least in the anterior-posterior direction by extending the tension arms or control guides 145, 146 which extend from inner catheter 50 (See also FIG. 21). Control arms 145, 146 include control hands 150a and 150b which connect to device 20 at anterior and posterior positioning control points 37 and 38 as described below. Tissue attachment members 40 further secure device 20 to tissue at annulus 8 and operate to assist in closure of gap 18. When device 20 is positioned or repositioned into desired location about annulus 8, tension is released from control arms 145, 146. When tension is released from control arms 145, 146, device 20 reverts back to its set orientation as shown in FIG. 2, thereby reducing the anterior-posterior distance as compared to that of FIG. 14. Successive tensioning and release or tensioning of control arms 145, 146 and/or spreaders 140a, 140p, and repositioning of device 20 may occur until a desired positioning is achieved. Successive checks of the positioning may be conducted to determine the amount, if any, of regurgitation. For instance, checks may be undertaken via 3D Echography and Angiography. TEE (Transesophageal Echo) would also typically be used. When an acceptable level of regurgitation is achieved, the prosthesis delivery system 100 may be removed, leaving behind device 20.

Figure 15:
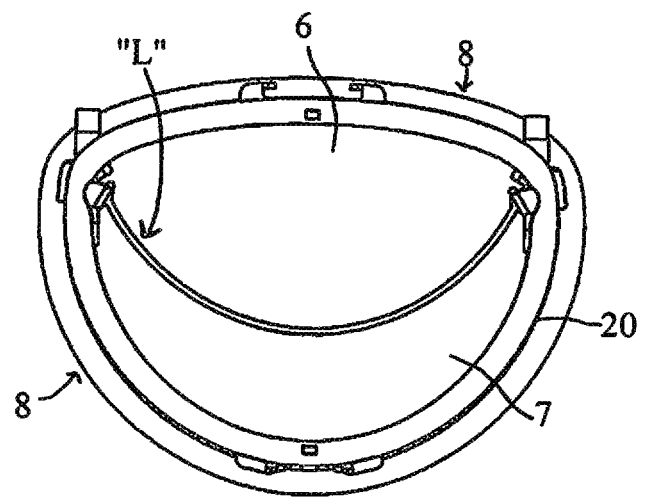
FIG. 15 is a diagram illustrating a top view of a further aspect of the present invention in conjunction with features of a heart valve.

FIG. 15 shows device 20 connected to valve 2 with prosthesis delivery system 100 removed. Relaxation of device 20 (i.e., allowing device 20 to return to its pre-set configuration shown in FIG. 2) in the anterior-posterior direction results in reduction or elimination of gap 18 and a desired line of coaptation "L". Such desired line of coaptation reduces or eliminates regurgitation.

Figure 23:
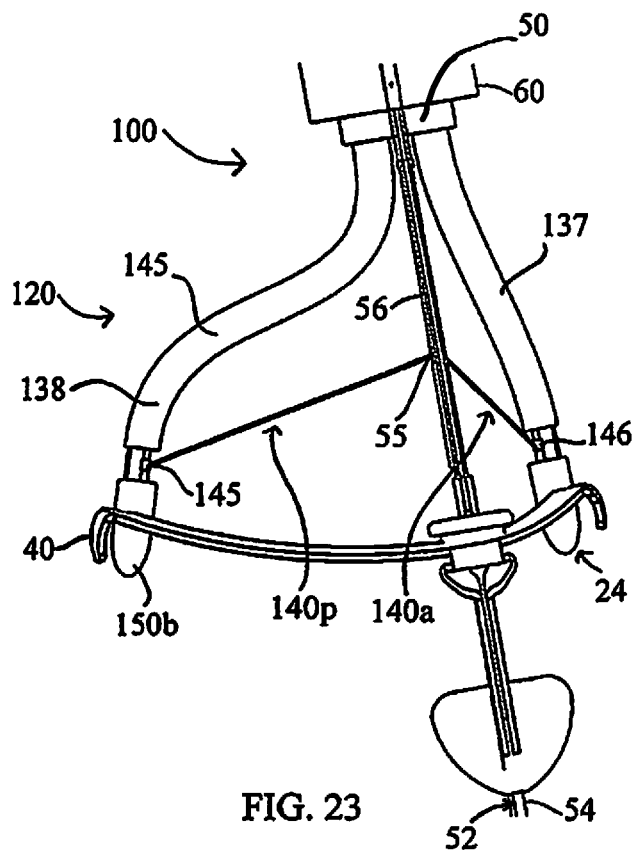
FIG. 23 is a diagram illustrating a close up view of a portion of a further aspect of the present invention.

A further aspect of the invention includes catheter-based prosthesis delivery system 100 for use in repairing a heart valve having leaflets and a valve annulus in a beating heart. With reference to FIGS. 11-28, system 100 includes a delivery catheter 60 with an annuloplasty ring, such as expandable annuloplasty ring 20, disposed at the distal end 61 of catheter 60. Catheter 60 is shown in the figures to be transparent for illustrative purposes. It may be appreciated that catheter 60 may be transparent or non-transparent. A nosecone 64 is positioned at a terminal end of capsule 62 and guidewire 52 runs through capsule 62 and nosecone 64. As addressed below, nosecone 64 is a split nosecone and comprises guideheads 210a and 210b. A distributor may be utilized as desired to allow free movement of wires and lumens and free movement of inner catheter 50 therethrough. Catheter 50 is configured to pass through catheter 60. Catheter 50 may be transparent or non-transparent. Catheter 50 is shown in the figures to be transparent for illustrative purposes. A variety of lumens and wires are configured to extend from the terminal end or terminal area of catheter 60 in the direction of Arrow A shown in FIG. 18. The commissural legs 30, 32 in catheter 60 are distal and positioned in the guideheads 210a, 210b in an extended state (i.e., legs 30, 32 are unfolded and extend generally straight as shown in FIG. 17 and FIG. 23). FIG. 17 is an illustration of device 20 positioned within catheter 60 with portions removed for clarity. Ring body 22 of device 20 extends generally in a loop toward inner catheter 50 in a space between catheter 50 and catheter 60 as shown in FIG. 17, for instance. More particularly, device 20 may be positioned generally between a terminal end of catheter 50 and a terminal end of catheter 60 with a portion of the legs 30, 32 extending past the terminal end of catheter 60 and into guidehead 210.

Figure 19:
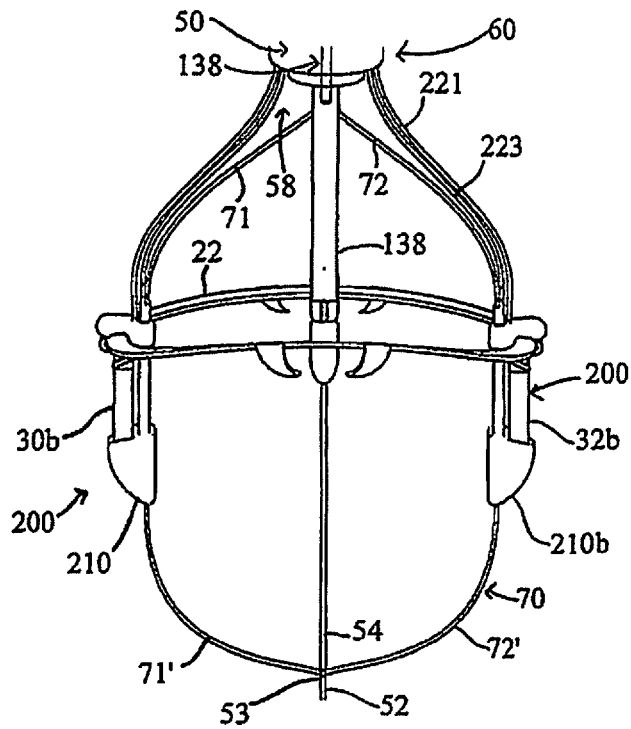
FIG. 19 is a diagram illustrating a perspective view of a further aspect of the present invention.
Figure 20:
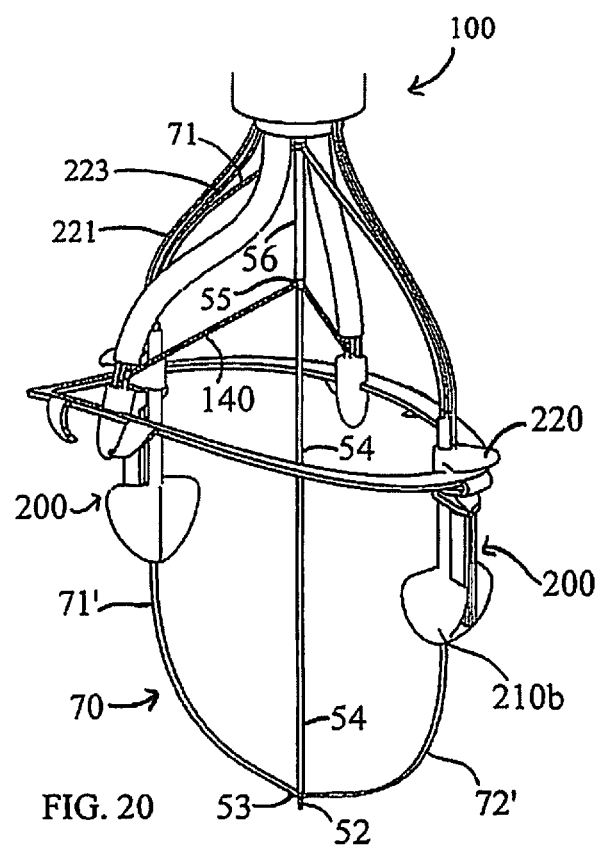
FIG. 20 is a diagram illustrating a perspective view of a further aspect of the present invention.

FIGS. 13, 19-28 depict various aspects of prosthesis delivery system 100 and commissure slide holder system 200 in conjunction with device 20. An orientation loop 70 is shown in FIG. 19 and includes upper segments 71, 72 leading to lower segments 71', 72' to form a loop-like structure. Segments 71', 72' are connected to a first orientation loop lumen 54 at orientation loop joint 53 (See also FIG. 27). Lumen 54 is positioned on guidewire 52 such that lumen 54 slides up and down along guidewire 52. As lumen 54 slides downward along guidewire 52, segments 71, 72 follow along with the lumen 54 to a position in the left ventricle and as shown in FIG. 13 and FIG. 19. In one aspect lumen 54 is nested within spreader lumen 56 as described below. In one aspect lumen 54 and spreader lumen 56 are nested within second orientation loop lumen 58. Segments 71, 72 are connected to lumen 58 at an orientation loop joint 57 (See for example FIG. 27). As lumen 58 is expressed in the direction of Arrow A, segments 71, 72 are pushed downward. By varying the distance between joint 53 and joint 57, the size and shape of orientation loop 70 may be manipulated. For instance, where joint 53 is positioned remotely from joint 57, loop 70 and segments 71, 71', 72, 72' will present a relatively narrow profile compared to when joint 53 is positioned more closely to joint 57 such that the segments 71, 72 will expand or radiate outward from lumen 54. When lumen 58 is extended downward while lumen 54 remains stationary, for instance, segments 71, 72 will bulge outward. In this manner the loop 70 can be adjusted to align with the respective commissure 14, 16 as shown in FIG. 11. As an operator slides lumen 54 upward, the orientation loop 70 bows outward, and as lumen 54 slides downward the orientation loop 70 narrows. The same narrowing and expanding control may be made by adjusting lumen 58 and the position of joint 57. When loop 70 is configured to a desired shape (i.e., so that segments 71, 72 are positioned at commissure 14, 16, for instance, device 20 may be expressed from catheter 60.

After guidewire 52 is inserted through gap 18 and introducer 82 has been positioned through fossa ovalis 15, catheter 60 is extended to a position immediately above valve 2. Thereafter orientation loop 70 is expressed from catheter 60 such that segments 71, 72 are positioned at respective commissure 14, 16 as shown in FIG. 11. Segments 71', 72' of orientation loop 70 extend downward from valve 2 into ventricle 13 as shown in FIG. 13, for instance. Orientation loop 70 is first used to orient the delivery system 200 to the mitral valve commissures and then used to orient or position respective commissure slide/holders 220 and guideheads 210.

Aspects of commissure slide holder system 200 are presented in FIGS. 19-22. System 200 includes a guidehead 210 and a holder 220. Guidehead 210 includes a leg slot 206 which is configured to receive a leg or legs 30, 32 of device 20. In one aspect guidehead 210 is connected to holder 220 by a slider 222. Slider 222 is configured to slide within holder 220. Holder 220 is configured to have a diameter such that a pair of adjacent and opposing holders 220 insert within catheter. Various configurations of holder 220 are possible. In one aspect holder 220 includes a slide groove 224 which receives slider 222. Slider 222 includes a loop segment channel configured to receive loop segment 72. Particularly, slider 222 is configured to slide upon orientation loop 70, particularly upon segment 72, 72'. Segment 72 runs through slider 222. A holder wire 221 connects to holder 220 and runs through the catheter 60 to handle for operation. A slider wire 223 connects to slider 220 and runs through the catheter 60 to a handle for operation. As orientation loop 70 is expressed from catheter 60, slide holder system 200 which is connected to loop 70 will also be expressed from catheter 60. System 200 travels downward along segment 72 into position as shown. Guidehead 210, slider 222, and the legs of device 20 which are positioned within slot 206 of guidehead 210 travel through gap 18 while body 22 of device 20 remains in the left atrium 10. When in position, an operator may slide guidehead 210 upward by holding holder 220 stationary and retracting slider wire 223 toward catheter 60. As slider 22 is pulled upward (passing through holder 220 at slide groove 224, for instance), guidehead 210 also slides upward. While guidehead 210 slides upward, legs 32 of device 20 will roll and/or fold to the memory position as described herein. An operator may make repeated sliding adjustments of slider 22 and guidehead 210 so that legs 32 are in a desired location and folded upon the underside of annulus 8. When guidehead 210a is fully lifted it may be appreciated that legs 32 are released from slot 206. Guidehead 210 may then be lifted upward through gap 18 by additional sliding action of slider 224 within holder 220 and/or by retracting the entirety of system 200 upward into catheter 60 by retracting the holder wire 221. A similar deploying of system 200 occurs with respect to guidehead 210a with a corresponding release of legs 30 and subsequent retraction of guidehead 210a and system 200 along segment 71 and into catheter 60. When legs 30, 32 are positioned at respective commissures 14, 15, as shown in FIG. 15, further manipulation of device 20 is undertaken as described herein.

Figure 24:
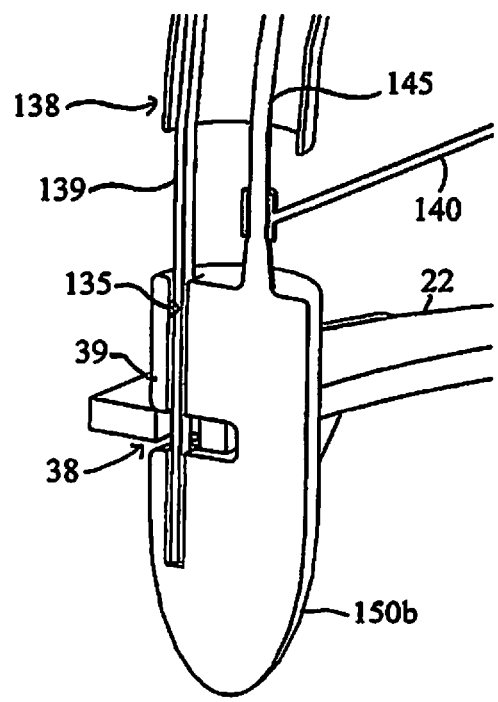
FIG. 24 is a diagram illustrating a close up section view of a portion of the delivery system of the present invention.

Prosthesis delivery system 100 includes a device flex mechanism 120. Flex mechanism 120 allows for the flexing of device 20 so that the tissue attachment members 40 may be selectively positioned to manipulate the annulus to improve valve function. Flex mechanism 120 flexes (i.e., expands or retracts) the device 20 in an anterior-posterior direction. As shown in FIG. 23 and FIG. 24, flex mechanism 120 includes control guide wires 145, 146. Guide wires 145, 146 lead to control hands 150a, 150b which in turn connect to device 20. Control wires 145, 146 are manipulated to exert a force upon device 20 to flex the device 20 as desired. An operator may insert or retract guide wires 145, 146 through catheter 50. In a further aspect, flex mechanism 120 includes spreader 140 which is also used to flex or manipulate device 20 as desired. In one aspect with respect to FIG. 23, a spreader 140p extends from a spreader joint 55 to control guide 145 or to control hand 150. Spreader 140p connects to posterior control hand 150b. An additional spreader such as spreader 140a may extend from spreader joint 55 to control guide 146 or control hand 150a. Spreader 140a connects to anterior control hand 150a. In one aspect spreader 140 is made of shape memory material (such as Nitanol) and having elastic property. Spreader 140 has sufficient rigidity to cause flex action of device 20 when spreader 140 is used to exert force against control guide 145, 146.

In one aspect spreader 140 is manipulated by adjustment of spreader lumen 56. Lumen 56 is nested within lumen 58 and slides upward or downward along lumen 54. Spreader 140 is connected to spreader lumen 56 at spreader joint 55. As lumen 56 extends downward along lumen 54, a force is exerted through spreader 140 to control guides 145, 146 to stretch device 20 in an anterior-posterior direction. Such stretch results in tissue attachment member 40 being repositioned outward so that member 40 may grab a more outer aspect of valve 2 in order for gap 18 to be closed when device 20 is unstressed. Flex mechanism 120 also includes a lock and release mechanism as described herein.

Device 20 is connected to prosthesis delivery system 100 at anterior and posterior control points 37, 38 (See FIG. 2). The connection at control points 37, 38 is utilized to spread or extend anterior portion 24 of device 20 away from posterior portion 26 in the anterior-posterior direction. This is done in order to manipulate the positioning of the tissue attachment members 40 upon the tissues of valve 2. Device 20 includes an anterior control point 37 and a posterior control point 38. In one aspect control points 37, 38 include a control port 39 (See FIG. 2 and FIG. 3). With reference to FIG. 24, control port 39 is configured to receive control pin 139 which extends from respective control lumens 137, 138. Control lumens assist in preventing or minimize wires from tangling in the delivery system 100. Control pin 139 extends through catheter 50 to a handle so that an operator may release control hand 150 from device 20 as noted herein. An anterior control lumen 137 and a posterior control lumen 138 (FIG. 23) are nested within catheter 50 to assist in holding or guiding control pin 138 and control guide 145 in position. In one aspect holding tubes 137, 138 extend partially into catheter 50.

Figure 17:
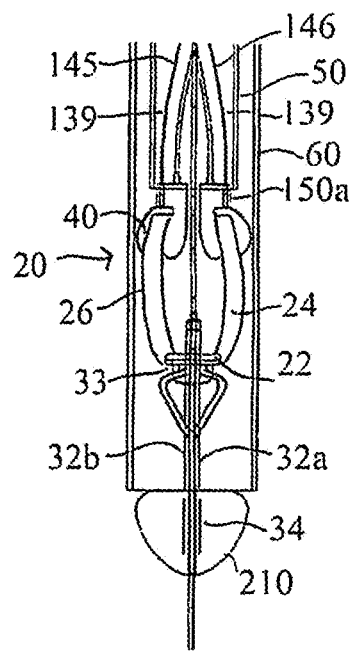
FIG. 17 is a diagram illustrating a front view of a further aspect of the present invention.
Figure 18:
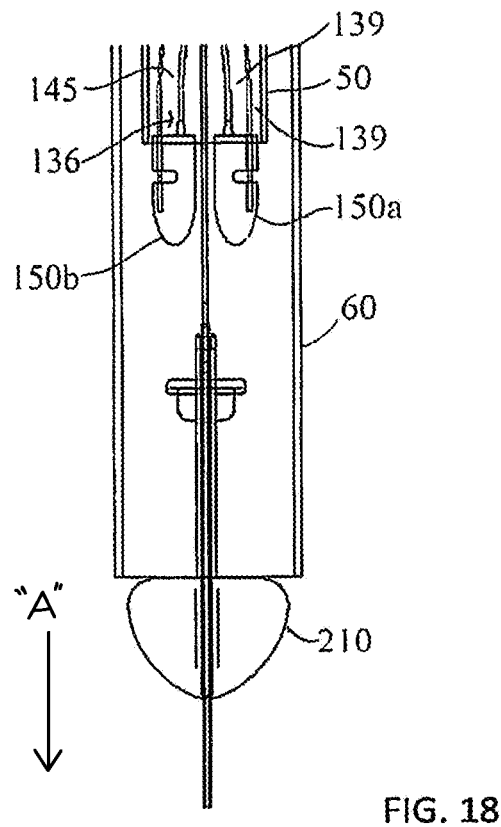
FIG. 18 is a diagram illustrating a front view of a further aspect of the present invention.

Control hand 150 includes a control slot 136 (See FIG. 18) in which is received ring body 22 at control point 37. While ring body 22 is positioned within control slot 136, control pin 139 is inserted (by extending control pin 139) through holding tube 138 and into pin channel 135 defined by hand 150. As control pin 139 passes along channel 135, control pin 139 inserts into control port 39. Device 20 is therefore selectively locked onto delivery system 100 at control hand 150. It may be appreciated that retraction of control pin 139 will remove pin 139 from control port 39 which will cause control hand 150 to release from control point 37. A similar control pin 139 is positioned within control port 39 at anterior control point 37. Other connecting means may be used to connect control guide 145 to device 20. It may be appreciated that when control hand 150 is locked onto device 20, and control hand 150 is retracted upward into or adjacent inner catheter 50) in the direction opposite arrow "A" as shown in FIG. 18), device 20, or a portion of device 20 will also be retracted or drawn into inner catheter 50. Alternatively, device 20 may be connected to control hand 150 such that no portion of device 20 extends into catheter 50 as shown in FIG. 17.

Figure 16:
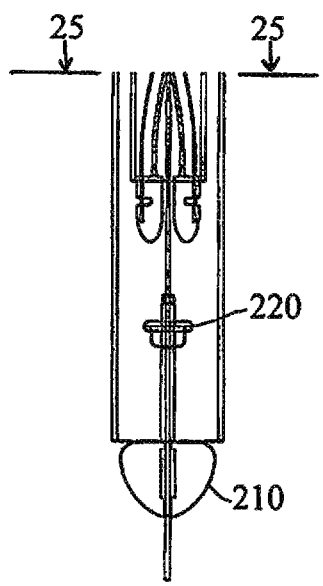
FIG. 16 is a diagram illustrating a front view of a further aspect of the present invention.
Figure 25:
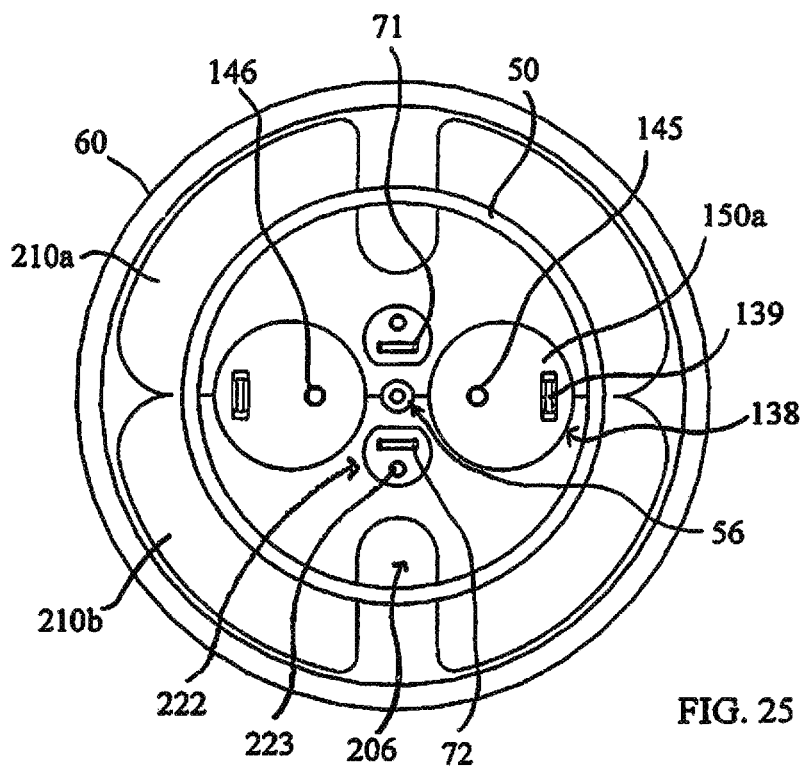
FIG. 25 is a diagram illustrating a section view taken along line 25-25 of FIG. 16 and with a portion removed for clarity.
Figure 26:
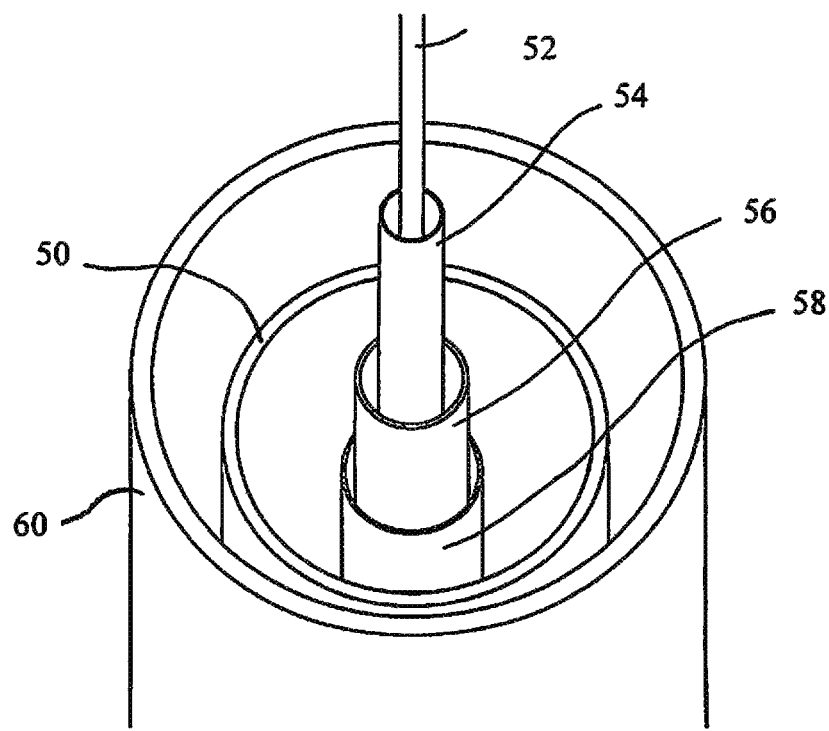
FIG. 26 is a diagram illustrating a partial perspective view of a portion of the aspects shown in FIG. 25.
Figure 27:
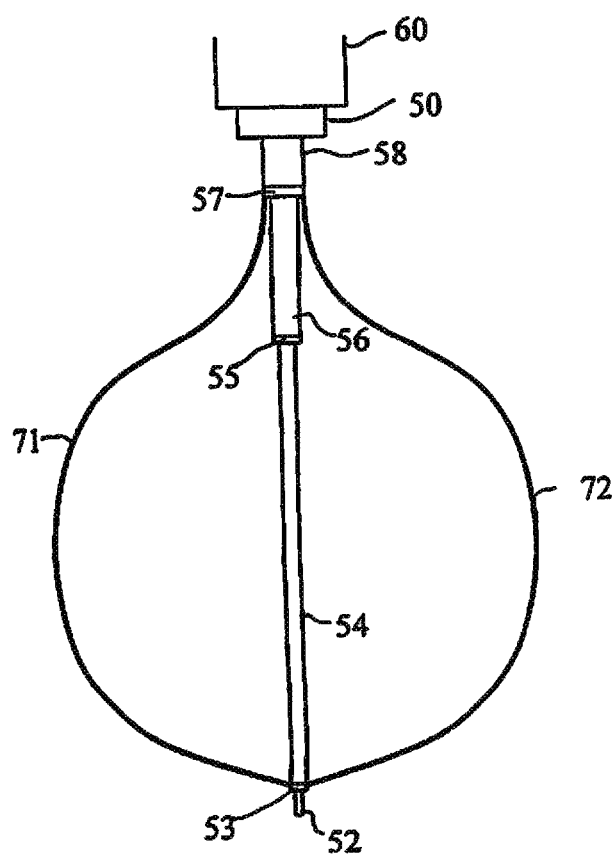
FIG. 27 is a diagram illustrating a partial front view of a further aspect of the present invention with portions removed for clarity.

FIG. 25 is a diagram illustrating a section view taken along line 25-25 of FIG. 16. Holder 220 is removed from view of FIG. 25 for clarity. An alternative distributor may be positioned upstream of view shown in FIG. 25, such that the distributor may receive the various lumens and control wires for maintaining efficient positioning of such elements. In the center of FIG. 25 is depicted the guidewire 52. FIG. 26 depicts a partial view of the center area of the view shown in FIG. 25. Nested about guidewire 52 is first orientation loop lumen 54 (which functions as lumen for guidewire 52 and connects with the distal end of orientation loop 70), spreader lumen 56, and second orientation lumen 58 (to which connects the proximal portion of the orientation loop 70). Such lumens are representative in nature and the various thicknesses and spaces between the respective lumens may be altered. The various lumens are shown in partial or cut-away view for clarity. In one aspect the lumens are slip-fit over each other. FIG. 27 illustrates the guidewire 52 and various lumens 54, 56, 58 as a representative orientation, together with inner catheter 50 and catheter 60. It may be appreciated that the arrangement of FIG. 27 is not presented in scale, and guideheads 210. Commissure slide holder system 200 and spreader 140 and control hands 150 are also removed from FIG. 27 for clarity.

The distal end of orientation loop 70 is connected to first orientation loop lumen 54 at distal end of lumen 54. In one aspect, loop segments 71, 72 are connected to and/or form orientation loop joint 53. In one aspect, loop joint 53 may be a band or other structure to which segments 71, 72 are connected, which joint 53 is in turn connected, via crimping, adhesion or other connection, to lumen 54. In alternatives, joint 53 may be integrally formed with segments 71, 72 and/or integrally formed with lumen 54. In other aspects, segments 71, 72 may be integrally formed directly with lumen 54 at joint 53 and/or otherwise part of lumen 54 or connected to lumen 54. The proximal end of loop 70 is connected to a distal end of second orientation loop lumen 58. In one aspect, loop segments 71, 72 are connected to and/or form orientation loop joint 57. In one aspect, loop joint 57 may be a band or other structure to which segments 71, 72 are connected, which joint 57 is in turn connected, via crimping, adhesion or other connection, to lumen 58. In alternatives, joint 57 may be integrally formed with segments 71, 72 and/or integrally formed with lumen 58. In other aspects, segments 71, 72 may be integrally formed directly with lumen 58 at joint 57 and/or otherwise part of lumen 58 or connected to lumen 58.

In one aspect spreaders 140 are connected to a distal end of spreader lumen 56. In one aspect, spreaders 140 are connected to and/or form spreader joint 55. In one aspect, joint 55 may be a band or other structure to which spreaders 140 are connected, which joint 55 is in turn connected, via crimping, adhesion or other connection, to lumen 56. In alternatives, joint 55 may be integrally formed with spreaders 140 and/or integrally formed with lumen 56. In other aspects, spreaders 140 may be integrally formed directly with lumen 56 at joint 55 and/or otherwise part of lumen 56 or connected to lumen 56. A spreader 140 is not depicted in FIG. 27 because it would typically extend perpendicular toward the viewer.

Figure 28:
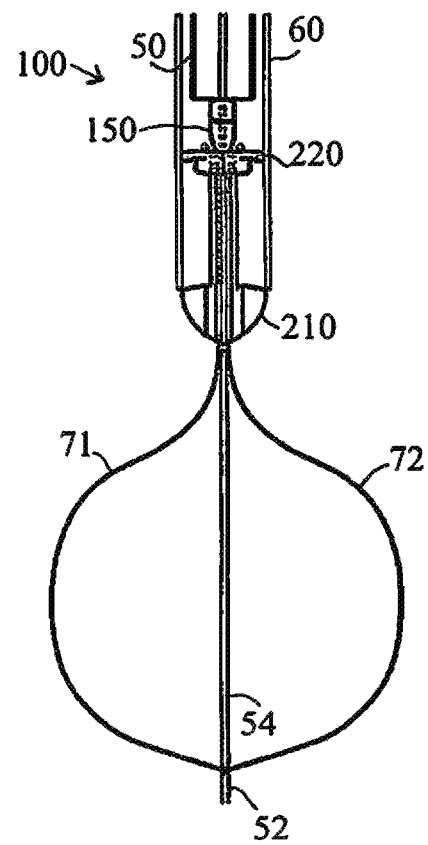
FIG. 28 is a diagram illustrating a partial front view of a further aspect of the delivery system of the present invention.

FIG. 28 depicts system 100 and shows guideheads 210 in relation to orientation loop segments 71, 72. It may be appreciated that orientation loop 70 may be adjusted to a variety of configurations by manipulation of the various lumens. Guideheads 210 extend from catheter 60 and ride along segments 71, 72 as a track for positioning within the heart valve as described herein.

In further reference to FIG. 17, device 20, having been subjected to an ice bath to make device 20 more easily pliable, is folded into the position generally as shown. In one aspect control hands 50 are first connected to device 20 at control points 37, 38, and then device 20 is fed into catheter 60 with legs 30, 32 extended within guideheads 201*a*, 210*b*. A loading tool, jigs or holding mechanism may be used to fold device 20 (within or adjacent an ice bath) for ease of folding device 20, ease of attaching device 20 to system 100, and/or ease of insertion of device 20 into catheter 60.

It may be appreciated that in some situations a patient's heart valve may be incapable of receiving device 20 or for other reasons device 20 is not appropriate for use in the particular patient, such as where a different size or configuration of device 20 is warranted. Such information might not be known or discovered until device 20 is expressed from catheter 60. In one aspect of the invention, device 20 may be retracted back into catheter 60. This allows the surgeon an opportunity to remove device 20 and/or use a different device 20 as desired. A surgeon may make repeated attempts to place device 20 into position and make repeated checks whether regurgitation is eliminated or reduced. If a successful result is not possible the surgeon may remove device 20 (i.e., by not having fully released or attached device 20 to the annulus, the legs 30 may be straightened by sliding guideheads downward along slider 22 and utilizing spreaders 140 to manipulate the ring body 22 to detach tissue attachment members 40 so that device 20 may be retracted back into catheter 60.

Device 20 may include a coating to assist in protection of the device and/or securing or adhering device 20 to tissues and/or as a lubricant to assist in release of device from the delivery system. Device 20 may be implanted adjacent the annulus of mitral valve 2. Device 20, or modified aspects of device 20, may also be implanted adjacent the annulus of tricuspid valve 3, the tricuspid valve having an anterior leaflet, posterior leaflet and septal leaflet, for instance. In further aspects it may be appreciated that the herein described systems include means for orienting the device 20 with ring body adjacent the annulus and such that the commissural legs are positioned in the ventricle; means for releasing the legs to furl into position within the ventricle and assist in support of the device 20 adjacent the annulus; means for furling and unfurling the legs for desired adjustment and placement or replacement within the ventricle; means for extending and retracting the device 20 so as to allow tissue attachment means to attach to the tissues of the heart valve; means for connecting and/or disconnecting control wires from the device to allow the device to remain in the heart; means for expressing the device into the heart chamber and also retracting the device back into a catheter for removal of the device 20 from the heart; among other means in light of the disclosure.

In a further aspect the invention comprises a method of repairing a heart valve 2 having leaflets 6, 7, and a valve annulus 8, the method comprising delivering a prosthesis 20 having a ring body 22 and self-folding commissure legs 30, 32 to a location adjacent to the heart valve 2, the legs 30, 32 extending between the leaflets 6, 7, and releasing the self-folding legs 30, 32, thereby causing the legs to be positioned at an underside (ventricle) of the heart valve while the ring body 22 is positioned at an upper side (atrium) of the heart valve.

It should be understood, of course, that the foregoing relates to exemplary embodiments of the invention and that modifications may be made without departing from the spirit and scope of the invention as set forth in the following claims.

What is claimed is:

1. A system, comprising:
   an orientation loop contacting a terminal end of a first lumen and contacting a terminal end of a second lumen, at least a portion of the first lumen disposed within the second lumen; and
   a first guidehead directly connected to the orientation loop.

2. The system of claim 1 where the orientation loop is joined to the terminal end of the first lumen and joined to the terminal end of the second lumen and includes a first segment and a second segment, the first guidehead slidably connected to the first segment, and further comprising a second guidehead connected to the second segment, each guidehead configured to receive a portion of a prosthesis for implantation at a heart valve.

3. The system of claim 1 where the second lumen is disposed within a catheter having a nose cone, the first guidehead comprising at least a portion of the nose cone.

4. The system of claim 1 where the orientation loop includes a first segment having a generally rectangular cross-section and a second segment having a generally rectangular cross-section, a slider integrally connected to the first guidehead having a loop segment channel, the first segment passing through the loop segment channel.

5. The system of claim 1 where the first guidehead is part of a prosthesis holder system configured to slide along the orientation loop for placement of a prosthesis adjacent a heart valve.

6. The system of claim 5 where the prosthesis holder system includes a holder having a slide groove in which slides a slider connected to the first guidehead, a first segment of the orientation loop passing through the slider.

7. The system of claim 5 where the prosthesis holder system includes a holder, the first guidehead configured to slide toward and away from the holder to fold or furl and unfold or unfurl legs of the prosthesis positionable within the guidehead.

8. The system of claim 5 where the holder system is configured to fold or furl and unfold or unfurl legs of the prosthesis for positioning and repositioning the legs.

9. The system of claim 1 further comprising, the orientation loop configured to bow outward upon adjustment of the first lumen relative the second lumen in a first direction and narrows inward upon adjustment of the first lumen relative the second lumen in a second direction opposite the first direction.

10. A system, comprising:
an orientation loop contacting a terminal end of a first lumen and connected to a terminal end of a second lumen, at least a portion of the first lumen disposed within the second lumen; and
a first guidehead connected to the orientation loop where the orientation loop includes a first segment and a second segment, the first guidehead slidably connected to the first segment, and further comprising a second guidehead connected to the second segment, the first guidehead and the second guidehead together forming a nose cone positioned at a terminal end of a catheter for delivering a prosthesis.

11. A system, comprising:
an orientation loop fastened to a first lumen and fastened to a second lumen, at least a portion of the first lumen disposed within the second lumen; and
a prosthesis holder system configured to slide along the orientation loop for placement of a prosthesis adjacent a heart valve.

12. The system of claim 11 where the prosthesis holder system includes a holder and a guidehead, the guidehead configured to slide toward and away from the holder to fold or furl and unfold or unfurl commissure legs of the prosthesis positionable within the guidehead.

13. The system of claim 11 where the prosthesis holder system includes a first holder and a first guidehead and a second holder and a second guidehead, the second holder and the second guidehead configured to operate independently of the first holder and the first guidehead in order to position and/or reposition legs of the prosthesis.

14. The system of claim 11 further comprising a prosthesis connected to the prosthesis holder system.

15. The system of claim 11 where the orientation loop is joined to the terminal end of the first lumen and joined to the terminal end of the second lumen and includes a first segment having a generally rectangular cross-section, the prosthesis holder system includes a guidehead slidable along the first segment.

16. The system of claim 11 further comprising a spreader lumen positioned between the first lumen and the second lumen.

17. The system of claim 16 where a spreader is connected at a terminal end of the spreader lumen at one end of the spreader and to a control guide at an opposite end of the spreader, the control guide configured to adjust the prosthesis.

18. A prosthesis delivery system for delivering a prosthesis adjacent an annulus of a heart valve of a heart, the heart having an atrium and a ventricle, the system comprising:
a catheter configured to be positioned within the atrium;
an orientation loop fastened to a first lumen and fastened to a second lumen, at least a portion of the first lumen disposed within the second lumen, the orientation loop configured to be expressed from the catheter and configured such that a portion of the orientation loop is deliverable through the heart valve to the ventricle such that a first segment of the orientation loop is configured to be oriented at a first commissure of the heart valve while a second segment of the orientation loop is configured to be oriented at a second commissure of the heart valve; and
a prosthesis holder system configured to utilize the orientation loop for placement of the prosthesis adjacent the heart valve, such that the first and the second segments are capable of being positioned at the commissures while the prosthesis is placed.

19. The delivery system of claim 18 where the prosthesis holder system includes a guide configured to hold a leg of the prosthesis in an extended state such that the leg may be placed through the annulus of the heart valve and into the ventricle.

20. The delivery system of claim 19 where the guide adjusts to allow the leg to release from the guide so the leg may be folded or furled within the ventricle while a ring of the prosthesis is located in the atrium.

21. The delivery system of claim 18 where the holder system adjusts to fold or furl and unfold or unfurl commissure legs of the prosthesis for positioning and repositioning the legs, the holder system further configured to retract the prosthesis into the catheter.

22. The delivery system of claim 18 further comprising a spreader configured to expand and retract the prosthesis.

23. The delivery system of claim 18 further comprising a device flex mechanism configured to flex a ring body of the prosthesis in an anterior-posterior direction.

24. The delivery system of claim 18 where the prosthesis holder system includes a split nose cone, the nose cone serving as a guide to travel to the annulus, and in a split configuration, to traverse anterolateral and posteromedial commissures independently.

25. The delivery system of claim 18 further comprising the prosthesis, the holder system configured to pass through a central lumen of the prosthesis.

26. The delivery system of claim 18 where the first segment bows away from the second segment, the first segment and the second segment define a reference plane transverse a plane generally defined by the annulus of the heart valve.

27. A system, comprising:
an orientation loop affixed to a distal end of a first lumen and affixed to a distal end of a second lumen, at least a portion of the first lumen disposed within the second lumen, the orientation loop bows outward upon adjustment of the first lumen relative the second lumen in a first direction and narrows inward upon adjustment of the first lumen relative the second lumen in a second direction opposite the first direction.

28. The system of claim 27 further comprising, the orientation loop having a first segment and a second segment, portions of the first segment extend away from portions of the second segment when a distance between a terminal end of the first lumen and a terminal end of the second lumen shortens.

29. The system of claim 27 where the orientation loop is joined to a terminal end of the first lumen and joined to an end portion of the second lumen.

30. The system of claim 27 further comprising a first guidehead connected to the orientation loop.

31. The system of claim 27 where the orientation loop includes a first segment and a second segment, portions of the first segment extend away from the second segment, the first segment and the second segment define a reference plane transverse a plane generally defined by an annulus of a heart valve through which the orientation loop is configured to pass.

32. A system, comprising:
an orientation loop affixed to a distal portion of a first lumen and affixed to a distal portion of a second lumen, at least a portion of the first lumen disposed within the second lumen, the first lumen and second lumen configured to allow a guide wire to pass along a central axis of the first lumen and of the second lumen; and a first guidehead connected to the orientation loop.

33. The system of claim 32 where the orientation loop originates at a distal end of the second lumen and terminates at a distal end of the first lumen.

34. The system of claim 32 further comprising a spreader lumen, the first lumen slides within the spreader lumen, the spreader lumen slides within the second lumen.

35. The system of claim 32 where at least a portion of the first lumen is always extended from the second lumen.

36. The system of claim 32 where the orientation loop is configured to fully retract into a catheter upon disconnecting from a prosthesis.

37. A system, comprising:

an orientation loop fastened to a first lumen and fastened to a second lumen, at least a portion of the first lumen disposed within the second lumen, the first lumen and the second lumen configured to allow a guide wire to pass along a central axis of the first lumen and the second lumen.

\* \* \* \* \*